(12) United States Patent
Chang et al.

(10) Patent No.: US 10,299,731 B2
(45) Date of Patent: May 28, 2019

(54) OBJECT POSE MEASUREMENT SYSTEM BASED ON MEMS IMU AND METHOD THEREOF

(71) Applicant: National Tsing Hua University, Hsinchu (TW)

(72) Inventors: Hsien-Ting Chang, Hsinchu (TW); Jen-Yuan Chang, Hsinchu (TW)

(73) Assignee: National Tsing Hua University, Hsinchu (TW)

( * ) Notice: Subject to any disclaimer, the term of this patent is extended or adjusted under 35 U.S.C. 154(b) by 159 days.

(21) Appl. No.: 15/586,342

(22) Filed: May 4, 2017

(65) Prior Publication Data

US 2018/0231374 A1   Aug. 16, 2018

(30) Foreign Application Priority Data

Feb. 13, 2017  (TW) .............................. 106104574 A

(51) Int. Cl.
| | |
|---|---|
| *G01B 21/00* | (2006.01) |
| *A61B 5/11* | (2006.01) |
| *A61B 5/00* | (2006.01) |
| *G01C 1/00* | (2006.01) |

(52) U.S. Cl.
CPC .......... *A61B 5/7203* (2013.01); *A61B 5/1116* (2013.01); *A61B 5/1121* (2013.01); *G01C 1/00* (2013.01); *A61B 2560/0223* (2013.01); *A61B 2562/028* (2013.01); *A61B 2562/0219* (2013.01); *A61B 2562/0223* (2013.01)

(58) Field of Classification Search
CPC .... A61B 2560/0223; A61B 2562/0219; A61B 2562/0223; A61B 2562/028; A61B 5/1121; A61B 5/7203; G01C 1/00
USPC .............. 702/85, 94, 95, 141, 151; 345/158; 600/424
See application file for complete search history.

(56) References Cited

U.S. PATENT DOCUMENTS

| | | | |
|---|---|---|---|
| 2017/0273665 A1* | 9/2017 | Kapoor | .................. A61B 90/39 |
| 2019/0011709 A1* | 1/2019 | Yadav | ................ G02B 27/0172 |

* cited by examiner

*Primary Examiner* — John H Le
(74) *Attorney, Agent, or Firm* — Lin & Associates Intellectual Property, Inc.

(57) ABSTRACT

An object pose measurement system based on MEMS IMU includes: an accelerometer, a magnetometer, a gyroscope, an object vector information calculation unit, and a rotation compensation unit; wherein the object vector information calculation unit is connected respectively to the accelerometer, magnetometer, gyroscope to receive respective measurement data and calculate object vector information; the rotation compensation unit is connected to the object vector information calculation unit to receive the object vector information, compute and output rotation compensated object vector information; wherein the rotation compensation unit performs quaternion rotation compensation computation and outputs the rotation compensated quaternion as the rotation compensated object vector information.

5 Claims, 2 Drawing Sheets

OBJECT POSE MEASUREMENT SYSTEM BASED ON MEMS IMU AND METHOD THEREOF

CROSS-REFERENCE TO RELATED APPLICATION

The present application is based on, and claims priority from Taiwan Patent Application No. 106104574 filed Feb. 13, 2017 the disclosure of which is hereby incorporated by reference herein in its entirety.

TECHNICAL FIELD

The technical field generally relates to an object pose measurement system and method, and in particular, to an object pose measurement system based on micro-electro-mechanical system (MEMS) inertial measurement unit (IMU) and method thereof.

BACKGROUND

Starting in 1908s, the optical measurement technology explored by the mechanical system with potentiometer as the human body joint angle measurement and the use of active tag opens up the research using the computer in the human body capture, and the mechanical and optical dynamic capture technology and equipment have gradually been developed. Then, the dynamic capture technology has attracted more and more attentions from the researchers and developers alike, as well as developed from the initial academic study gradually to the commercial realization. One of the important applications of the dynamic capture technology development is to be able to better capture the human body dynamic data to provide to the animation, film and television and other multimedia industries, to describe the near-real movement state to reduce production costs, as well as greatly enhance the production efficiency to achieve the entertainment effect, which is still the major commercial application for dynamic capture technology.

The conventional dynamic capture technology can be broadly divided into mechanical-based technology and optical-based technology; wherein the mechanical-based technology is for a user to wear a mechanical frame attached with encoder to record the rotation of the joints of the arm when the user moves the arm so as to learn the rotation of the arm joint movement. The advantage of this approach is the measured angle can be easily converted to the input required by the motor when applied to the humanoid robot arm. In contrast, optical-based dynamic capture technology is to use cameras disposed at different angles to track the marks placed on the subject, and then feed the tracking information back to the computer for a large and complex computation to learn the dynamic state of the target. In particular, since the 1980s after the rapid development of optical-based dynamic capture technology, the optical-based technology has been the mainstream choice in the market due to high precision characteristics. On the other hand, the shortcomings of optical dynamic capture technologies are that the range of motion of the subject must often be confined to a fixed range; otherwise the line-of-sight might be shielded.

However, with the micro-electro-mechanical system (MEMS) technology breakthroughs and the rise of related industries, an approach to use inertial measurement unit (IMU) for dynamic data capture has emerged. In general, the IMU includes three kinds of sensors, that is, an accelerator, a gyroscope and a magnetometer. The chip is not only small in size but also low in price, which constitutes a major feature of the technology. The principle of IMU-based dynamic capture technology is the application of IMU to obtain the acceleration, angular velocity and magnetic field strength information, which is processed by an algorithm to obtain the pose of the object in the space. Therefore, the processing of the acceleration, angular velocity and magnetic field strength information becomes extremely important when using this approach. The main reason is that the angular velocity measured by the gyroscope, even in the state where the entire IMU remains stationary, still has a certain degree of offset error, and the error will be accumulated after the integral operation in the algorithm. On the other hand, the magnetometer is also easily susceptible to the effects of the ferromagnetic environment, which in turn causes the read value to cause the offset. These are the natural defects that are unavoidable in the IMU. Regardless, from the perspective of volume, precision, cost, and immediacy, the IMU-based approach is still more appropriate than the mechanical-based or optical-based technologies when applied to measuring the pose of small objects in space.

With improved resolution precision of the dynamic capture system of human motion, the feasibility of using the technology as the measurement system significantly increases; therefore, the dynamic capture technology begins to extend to other application areas than only to entertainment, including medical rehabilitation, ergonomics, virtual reality, and industrial measurement and other fields. Relatively, the more and more widely application areas also place higher demands regarding resolution precision on the dynamic capture technology, which becomes an important issue on whether the industry can achieve successful commercialization.

SUMMARY

An embodiment of the present invention provides an object pose measurement system based on MEMS IMU, comprising: an accelerometer, a magnetometer, a gyroscope, an object vector information calculation unit, and a rotation compensation unit; wherein the object vector information calculation unit is respectively connected to the accelerometer, the magnetometer and the gyroscope to receive respective measurement data from the accelerometer, the magnetometer and the gyroscope and calculate object vector information; the rotation compensation unit connected to the object vector information calculation unit for receiving the object vector information, and computing and outputting a rotated object vector information after performing rotation compensation; wherein the object vector information calculation unit further comprising: a direction cosine matrix (DCM) module, a quaternion module, and a direction cosine matrix to quaternion (DCM-to-Quaternion) module; the DCM module respectively connected to the accelerometer and the magnetometer to establish a DCM; the DCM-to-Quaternion module connected to the DCM module to convert the DCM to a quaternion and transmit the quaternion to the rotation compensation unit; the quaternion module connected to the DCM-to-Quaternion module, the gyroscope, the rotation compensation unit for establishing and updating the quaternion; the rotation compensation unit connected to the DCM-to-Quaternion module and the quaternion module respectively for performing the rotation compensation operation on the quaternion and outputting a rotated quaternion after rotation compensation as the rotated object vector information after rotation compensation.

Another embodiment of the present invention provides an object pose measurement method based on MEMS IMU, applicable to an accelerometer, a magnetometer, and a gyroscope, comprising the steps of: receiving respective original measurement data from the accelerometer, the magnetometer and the gyroscope; calibrating signal scale and offset of the original measurement data; filtering noise out from the signal of the original measurement data; based on the calibrated measurement data of the accelerometer and the magnetometer and the orthogonal characteristics of gravity and magnetic north direction, establishing a direction cosine matrix (DCM), and converting the DCM into a representation of an accelerometer-and-magnetometer quaternion, and based on the calibrated measurement data from the gyroscope, establishing a gyroscope quaternion to indicate a rotation situation of the object in a body-fixed coordinate system, and then multiplying an inverse of a quaternion representing an object rotation pose with the gyroscope quaternion, executing inverse computation to obtain an actual rotational amount of the object in a global coordinate system; based on the inverse of converted gyroscope quaternion and the accelerometer-and-magnetometer quaternary, performing quaternion multiplication and calculating a rotation error; based on the rotation error, using a control theory to calculate a quaternion rotation compensation, and using the converted gyroscope quaternion and the rotation compensation amount to perform quaternion rotation compensation; updating the gyroscope quaternion; and, outputting the object vector information based on the updated gyroscope quaternion.

The foregoing will become better understood from a careful reading of a detailed description provided herein below with appropriate reference to the accompanying drawings.

BRIEF DESCRIPTION OF THE DRAWINGS

The embodiments can be understood in more detail by reading the subsequent detailed description in conjunction with the examples and references made to the accompanying drawings, wherein.

DETAILED DESCRIPTION OF THE DISCLOSED EMBODIMENTS

Figure 1:
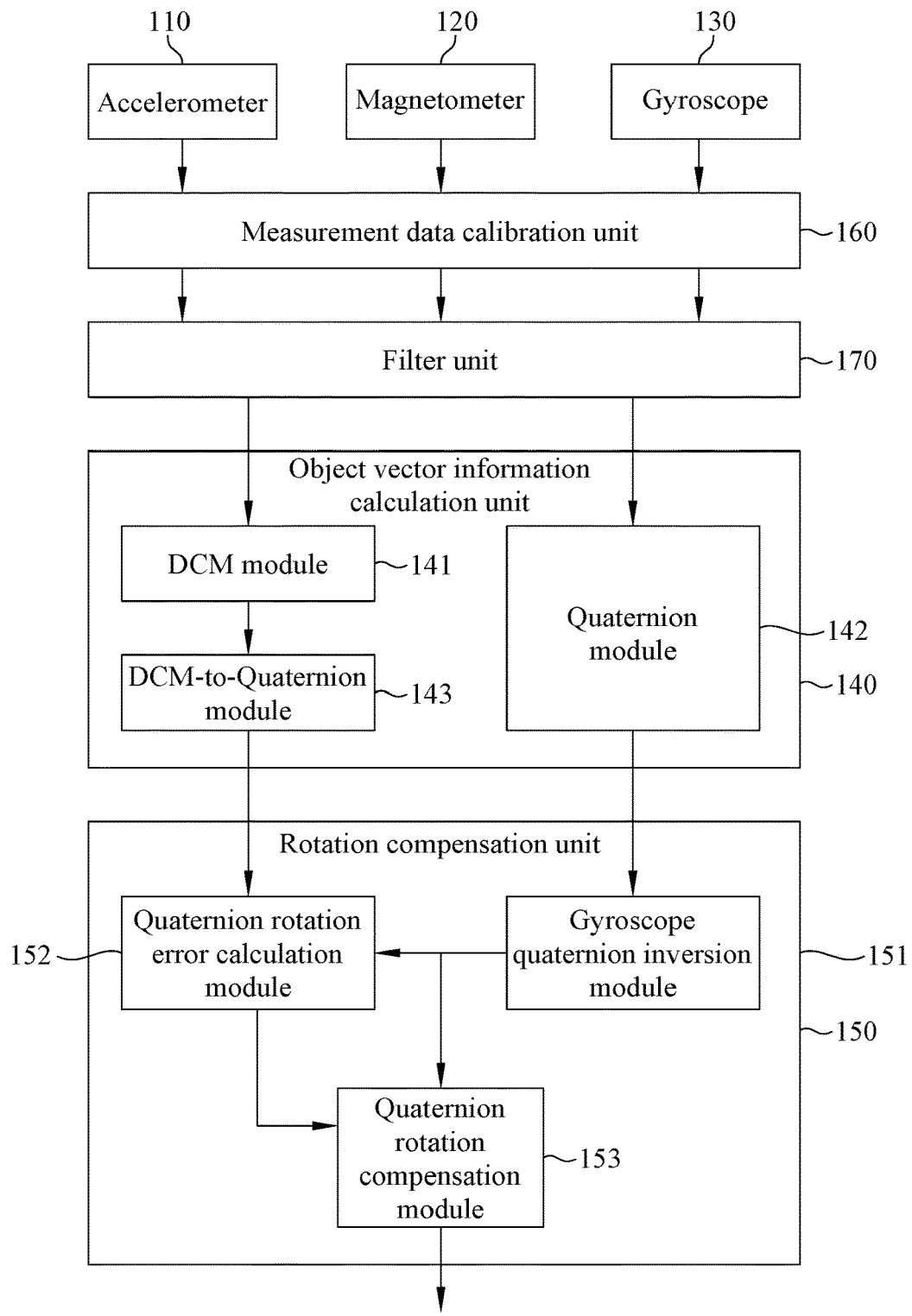
FIG. 1 shows a schematic view of an object pose measurement system based on MEMS IMU in accordance with an exemplary embodiment.

FIG. 1 shows a schematic view of an object pose measurement system based on MEMS IMU according to the present invention. As shown in FIG. 1, the object pose measurement system based on MEMS IMU of the present invention comprises: an accelerometer 110, a magnetometer 120, a gyroscope 130, an object vector information calculation unit 140, and a rotation compensation unit 150; wherein the object vector information calculation unit 140 is respectively connected to the accelerometer 110, the magnetometer 120 and the gyroscope 130 to receive respective measurement data from the accelerometer 110, the magnetometer 120 and the gyroscope 130 and calculate object vector information; the rotation compensation unit 150 is connected to the object vector information calculation unit 140 for receiving the object vector information, and computing and outputting rotated object vector information after performing rotation compensation.

Accordingly, the object vector information calculation unit 140 further comprises: a direction cosine matrix (DCM) module 141, a quaternion module 142, and a direction cosine matrix to quaternion (DCM-to-Quaternion) module 143; wherein the DCM module 141 is respectively connected to the accelerometer 110 and the magnetometer 120 to establish a DCM; the DCM-to-Quaternion module 143 is connected to the DCM module 141 to convert the DCM to a quaternion and transmits to the rotation compensation unit 10; the quaternion module 142 is connected to the DCM-to-Quaternion module 143, the gyroscope 130, and the rotation compensation unit 150 for establishing and updating the quaternion; the rotation compensation unit 150 is connected to the DCM-to-Quaternion module 143 and the quaternion module 142 respectively for performing the rotation compensation operation on the quaternion and outputting a rotated quaternion after rotation compensation as the rotated object vector information after rotation compensation.

It should be noted that the object pose measurement system may further comprise a measurement data calibration unit 160, connected respectively to the accelerometer 110, the magnetometer 120 and the gyroscope 130, and the object vector information calculation unit 140. The measurement data calibration unit 160 first calibrates the respective original measurement data from the accelerometer 110, the magnetometer 120, and the gyroscope 130 for the offset and the signal scale, and then the object vector information calculation unit 140 calculates the object vector information.

Moreover, the object pose measurement system may further comprise a filter unit 170, for low-pass filtering of the accelerometer 110 and the magnetometer 120 to achieve calibration of magnetic dip angle. The calibrated result is then used by the DCM module 141 to establish a direction cosine matrix (DCM). The filter unit 170 also performs high-pass filtering on the gyroscope 130 at the same time to perform an integral operation, and the result is used by the quaternion module 142 to establish a gyroscope quaternion; wherein the DCM passes through the DCM-to-Quaternion module 143 and is converted into an accelerometer-and-magnetometer quaternion.

The rotation compensation unit 150 may further comprise a gyroscope quaternion inversion module 151, a quaternion rotation error calculation module 152, and a quaternion rotation compensation module 153; wherein the gyroscope quaternion inversion module 151 is connected to the quaternion module 142 to perform an inverse conversion operation on the gyroscope quaternion; the quaternion rotation error calculation module 152 is connected to the gyroscope quaternion inversion module 151 and the DCM-to-Quaternion module 143 to perform quaternion multiplication and calculate the rotation error based on the gyroscope quaternion after the inverse conversion operation and the accelerometer-and-magnetometer quaternion; and, the quaternion rotation compensation module 153 is connected respectively to the gyroscope quaternion inversion module 151 and the quaternion rotation error calculation module 152, and performs the quaternion rotation compensation based on the inversed gyroscope quaternion and the rotation error. The quaternion module 142 updates the quaternion based on the quaternion after the rotation compensation, and then outputs the rotation compensated object vector information.

Figure 2:
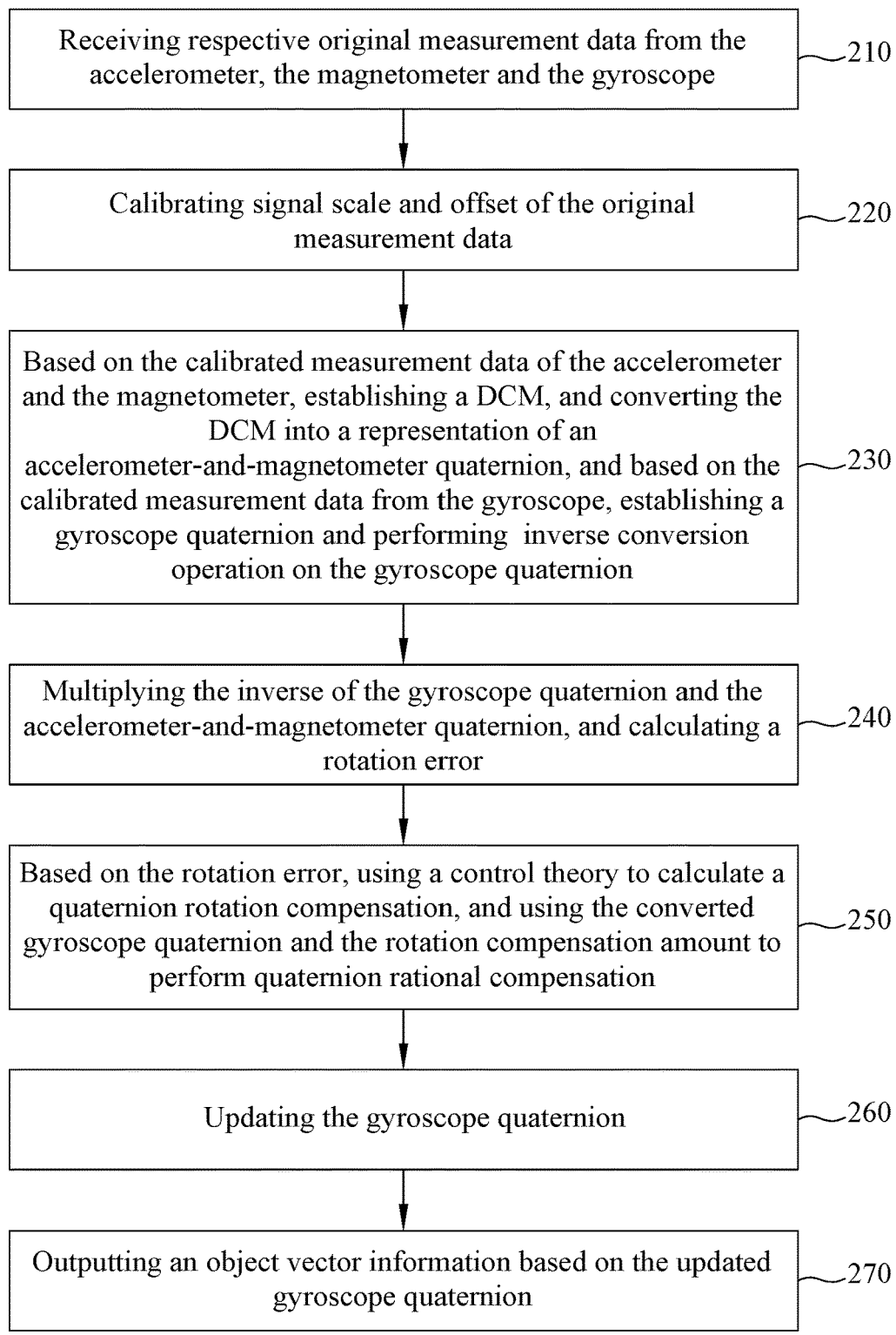
FIG. 2 shows a flowchart of an object pose measurement method based on MEMS IMU in accordance with an exemplary embodiment.

FIG. 2 shows a flowchart of an object pose measurement method based on MEMS IMU in accordance with an exemplary embodiment. As shown in FIG. 2, the object pose measurement method based on MEMS IMU of the present invention, which is applicable to an accelerometer, a magnetometer, and a gyroscope, comprises the steps of: receiving respective original measurement data from the accelerometer, the magnetometer and the gyroscope (step 210); calibrating signal scale and offset of the original measurement data (step 220); based on the calibrated measurement data of the accelerometer and the magnetometer, establishing a direction cosine matrix (DCM), and converting the DCM into a representation of an accelerometer-and-magnetometer quaternion, and based on the calibrated measurement data from the gyroscope, establishing a gyroscope quaternion and performing inverse conversion operation on the gyroscope quaternion (step 230); multiplying the inverse of the gyroscope quaternion and the accelerometer-and-magnetometer quaternary, and calculating a rotation error (step 240); based on the rotation error, using a control theory to calculate a quaternion rotation compensation amount, and using the inverse of the gyroscope quaternion and the quaternion rotation compensation amount to perform quaternion ration compensation (step 250); updating the gyroscope quaternion (step 260); and, outputting object vector information based on the updated gyroscope quaternion (step 270).

It should be noted that in step 220, in addition to calibrating the signal scale and the offset of the original measurement data, the step may further comprises a step of filtering noise out from the signal of the original measurement data. In step 230, because the pose of an object in space can be represented by a three-element vector, the relationship between the two vectors before and after rotation can be represented by a 3×3 matrix. The principle is that the gravity and magnetic north direction are orthogonal to each other, which is applied to the calibrated accelerometer and magnetometer measurement data to establish a direction cosine matrix. Nine elements are needed to describe the rotation matrix; however, these nine elements are not completely linear independent, so the actual rotation in space only needs four elements to express, in which a high-order complex expression can be used. Because when the quaternion multiplication and rotation error calculation are performed in step 240, the two inputs to the multiplication must have the same form, the rotation matrix must be converted into a quaternion form in advance. Furthermore, the gyroscope quaternion established according to the calibrated gyroscope measurement data is used to a rotation situation of the object in a body-fixed coordinate system; afterwards, the inverse of the quaternion representing the rotational pose of the object and the gyroscope quaternion must be multiplied to execute the inverse conversion operation to obtain the actual amount of rotation of the object in the global coordinate system.

In summary, the object pose measurement system of the present invention uses an IMU comprising an accelerometer, a magnetometer, and a gyroscope, to respectively measure the gravity, globe magnetic direction and the object rotational velocity; and then uses the two of the above three measurements to establish an object pose, and uses a mathematic model to perform rotation compensation to obtain the pose of the IMU in space. Then, the IMU is fixed to a rigid object to measure the pose of the object. Moreover, with a plurality of IMUs, it is possible to compute the relative positions among the objects, such as, spatial angle.

Hence, the object pose measurement system of the present invention can achieve the intended purpose and function by the skill of the invention, and conforms to the novelty, progress and industrial utilization of the invention patent.

It will be apparent to those skilled in the art that various modifications and variations can be made to the disclosed embodiments. It is intended that the specification and examples be considered as exemplary only, with a true scope of the disclosure being indicated by the following claims and their equivalents.

What is claimed is:

1. An object pose measurement method based on microelectro-mechanical system (MEMS) inertial measurement unit (IMU), comprising:
    receiving respective original measurement data of a pose of an object from an accelerometer, a magnetometer and a gyroscope;
    calibrating signal scale and offset of the original measurement data to generate calibrated measurement data respectively for the accelerometer, the magnetometer and the gyroscope;
    based on the calibrated measurement data of the accelerometer and the magnetometer, establishing a direction cosine matrix (DCM), and converting the DCM into a representation of an accelerometer-and-magnetometer quaternion, and based on the calibrated measurement data of the gyroscope, establishing a gyroscope quaternion and performing an inverse conversion operation on the gyroscope quaternion to generate an inverse of the gyroscope quaternion;
    multiplying the inverse of the gyroscope quaternion and the accelerometer-and-magnetometer quaternion to generate a rotation error;
    based on the rotation error, using a control theory to calculate a quaternion rotation compensation amount for compensating a rotation of the object, and using the inverse of the gyroscope quaternion and the quaternion rotation compensation amount to perform quaternion rotation compensation to generate a rotated quaternion; and
    outputting the rotated quaternion as rotation compensated object vector information.

2. The object pose measurement method based on MEMS IMU as claimed in claim 1, wherein the step of calibrating signal scale and offset of the original measurement data further comprises using a filter to filter out noise from the original measurement data.

3. The object pose measurement method based on MEMS IMU as claimed in claim 1, wherein characteristics of orthogonality between gravity and magnetic north direction is applied in establishing a DCM using the calibrated measurement data of the accelerometer and the magnetometer.

4. The object pose measurement method based on MEMS IMU as claimed in claim 1, wherein converting the DCM to an accelerometer-and-magnetometer quaternion is achieved with a rotation matrix.

5. The object pose measurement method based on MEMS IMU as claimed in claim 1, wherein the gyroscope quaternion established according to the calibrated measurement data of the gyroscope is used in a rotation situation of the object in a body-fixed coordinate system; afterwards, the inverse of the gyroscope quaternion representing a rotational pose of the object and the gyroscope quaternion must be multiplied to execute the inverse conversion operation to obtain an actual amount of rotation of the object in a global coordinate system.

* * * * *